United States Patent [19]
Lakowicz et al.

[11] Patent Number: 5,759,767
[45] Date of Patent: Jun. 2, 1998

[54] TWO-PHOTON AND MULTI-PHOTON MEASUREMENT OF ANALYTES IN ANIMAL AND HUMAN TISSUES AND FLUIDS

[75] Inventors: Joseph R. Lakowicz, 10037 Fox Den Rd., Ellicott City, Md. 21042; Thomas G. Burke, Lexington, Ky.; Ignacy Gryczynski, Baltimore; Henryk Malak, Ellicott City, both of Md.

[73] Assignee: Joseph R. Lakowicz, Ellicott City, Md.

[21] Appl. No.: 731,270

[22] Filed: Oct. 11, 1996

[51] Int. Cl.$^6$ .................. C12Q 1/00; G01N 33/567; G01N 33/53

[52] U.S. Cl. .................. 435/4; 435/7.21; 435/968; 436/63; 436/800; 356/4.01; 356/39; 250/200; 250/459.1; 250/338.1

[58] Field of Search .................. 435/4, 7.21, 968; 250/459.1, 338.1, 200; 356/4.01; 436/63, 800

[56] References Cited

U.S. PATENT DOCUMENTS

5,523,573  6/1996  Hanninen et al. .................. 250/459.1

OTHER PUBLICATIONS

Williams et al., "Two-photon molecular excitation provides intrinsic 3-dimensional resloution for laser-bsed microscopy and microphotchemistry," FASEB, Aug. 1994, 8, 804–813.1.

Bodaness et al., "The Two-photon Laser-induced Fluorescence of the Tumor-localizing Photosensitizer Hematoporphyrin Derivative," J.Biol. Chem. Sep. 15, 1986, 261, 12098–12101.

Sepaniak, Michael J., et al., "Laser Two-Photon Excited Fluorescence Detection . . . ," *Analytical Chemistry*, vol. 49, No. 11, pp. 1554–1556, Sep., 1977.

Wirth, M.J., et al., "Two–Photon Excited Molecular Fluorescence in Optically Dense Media . . . ," *Analytical Chemistry*, vol. 49, No. 13, pp. 2054–2057, Nov. 1977.

Steffen, Ray L., et al., "Multipoint Measurements in Optically Dense Media . . . ," *Analytica Chimica Acta*, 215 (1988) 203–210.

Denk, Winfried, et al., "Two–Photon Laser Scanning Fluorescence Microscopy," *Science*, vol. 248, pp. 73–76, Apr., 1990.

Birch, David J.S., et al., "Time–Domain Fluorescence Spectroscopy Using Time–Correlated Single–Photon Counting," *Topics in Fluorescence Spectroscopy, vol. 1: Techniques*, Joseph R. Lakowicz, ed., Plenum Press, New York, 1991, pp. 1–95.

Piston, David W., et al., "Time–Revealed Fluorescence Imaging and Background Rejection by Two–Photon Excitation in Laser Scanning Microscopy," School of Applied and Engineering Physics and Dept. of Physics, Cornell Univ., Ithaca, New York, SPIE, vol. 1640, *Time–Resolved Laser Spectroscopy in Biochemistry III* (1992)/379.

Huang, Zhengping, et al., "Theory for Two–Photon Excitation in Pattern Photobleaching with Evanescent Illumination," *Biophysical Chemistry*, 47 (1993), pp. 241–249.

(List continued on next page.)

*Primary Examiner*—Louise Leary
*Attorney, Agent, or Firm*—Rothwell, Figg, Ernst & Kurz, p.c.

[57] ABSTRACT

A method of measuring an analyte present in animal (e.g., human) tissue or fluids such as blood or plasma. The analyte is multi-photon excitable (e.g., two-photon excitable) at a first wavelength at which the animal tissue is substantially non-absorbing. The analyte fluoresces at a second wavelength upon being excited at the first wavelength. The animal tissue is irradiated with radiation at the first wavelength so as to excite the analyte through absorption by the analyte of two or more photons of the radiation at the first wavelength. Excitation of the analyte results in a fluorescent emission from the analyte of radiation at the second wavelength. The emission at the second wavelength is detected, and the concentration of analyte determined based on the detected emission.

22 Claims, 11 Drawing Sheets

OTHER PUBLICATIONS

Lakowicz, Joseph R., et al., "Tryptophan and Fluorescence Intensity and Anisotropy Decays of Human Serum Albumin Resulting from One–Photon and Two–Photon Excitation," *Biophysical Chemistry*, 45 (1992), pp. 1–6.

Lakowicz, J.R., et al., "time–Resolved Fluorescence Intensity and Anisotropy Decays of 2,5–Diphenyloxazole by Two–Photon Excitation and Frequency–Domain Fluorometry," American Chemical Society 1992, *J. of Physical Chemistry*, vol. 96, No. 7, pp. 3000–3006.

Lakowicz, Joseph R., et al., "Two Photon–Induced Fluorescence Intensity and Anisotropy Decays of Diphenylhexatriene in Solvents and Lipid Bilayers," *Journal of Fluoroescence*, vol. 2, No. 4, 1992, pp. 247–258.

TWO-PHOTON AND MULTI-PHOTON MEASUREMENT OF ANALYTES IN ANIMAL AND HUMAN TISSUES AND FLUIDS

BACKGROUND OF THE INVENTION

This work was supported by the NIH National Center for Research Resources and the National Cancer Institute.

1. Field of the Invention

This invention relates to the field of measuring analytes in a sample.

2. Description of the Background Art

It is desirable to measure the concentration of analytes, such as drugs, in human or animal tissue or fluid such as human blood. For example, treatment with certain drugs require careful control of the drug's concentration to assure effectiveness without excessive toxicity.

Certain drugs are known to display fluorescence when excited with one-photon at a wavelength below about 600 nm. However, such wavelengths are inconvenient for clinical monitoring because they are absorbed by tissues, including skin and blood. Such wavelengths also result in significant autofluorescence.

There remains a need in the art for methods for measuring analytes present in animal and human tissues and fluids.

SUMMARY OF THE INVENTION

In accordance with the present invention, a method of measuring an analyte present in animal (e.g., human) tissue (such as blood or plasma) comprises providing animal tissue containing an analyte which is multi-photon excitable (e.g., two-photon excitable) at a first wavelength at which the tissue is substantially non-absorbing, which analyte fluoresces at a second wavelength upon being excited at said first wavelength. The animal tissue is irradiated with radiation at said first wavelength so as to excite said analyte through absorption by said analyte of two or more photons of said radiation at said first wavelength, wherein excitation of said analyte results in a fluorescent emission from said analyte of radiation at the second wavelength. The emission at said second wavelength is detected, and the concentration of analyte is determined based on the detected emission.

DETAILED DESCRIPTION OF THE PREFERRED EMBODIMENTS

The present invention is directed to a method as outlined above of measuring an analyte, such as a drug, present in animal tissue which may include blood, plasma, or the like. It is intended that the term "animal" include the term "human", and that the term "animal tissue" include human tissue and fluids such as blood, plasma or the like. The present invention includes direct analyte measurements in whole blood and non-invasive detection of analytes through skin.

As outlined above, animal tissue containing an analyte is irradiated with light at a first wavelength so as to excite the analyte by multi-photon (e.g., two-photon) absorption of the first wavelength. The two-photon excitation causes the analyte to fluoresce, resulting in an emission at the second wavelength.

In preferred embodiments, the intensity of the emission at the second wavelength is measured. The concentration of the analyte can be determined utilizing the measured intensity of the emission.

In other embodiments, the lifetime of the emission of the second wavelength is measured. The concentration of the analyte can be determined utilizing the measured lifetime of the emission.

In preferred embodiments, the first wavelength is greater than about 400 nm, preferably greater than about 600 nm, more preferably greater than about 650 nm. Generally, the first wavelength is less than about 1,000 nm.

Typically, the second wavelength, at which the emission takes place, is generally less than about 1,000 nm.

The two-photon method of the present invention has significant advantages over utilization of a one-photon method. The present invention permits targeting the point of observation, such that emissions result only from "ballistic" photons. In contrast, with a one-photon method, emissions are received from many locations, not only where the light source (e.g., laser) is pointing as in the two-photon method of the present invention.

The invention is not limited to detection of drugs, but can be utilized to detect any fluorophore. For example, the invention can be utilized for measurement of a labeled substance, such as a peptide or hormone, where the material has been labeled with a fluorophore chosen for two-photon excitation. Thus, the invention is applicable to analytes which are a fluorescent substance of the type used in fluorescence measurements, such as fluorosceins, rhodamines, calcium-sensitive fluorophores such as Fura-2, pH-sensitive fluorophores such as the seminapthofluoresceins (SNAFLs) and seminapthorhodamines (SNARFs), sodium-sensitive fluorophores such as Sodium Green and sodium-binding benzofuran isophthalate (SBFI), potassium-sensitive fluorophores such as potassium-binding isophthalate (PBFI), cyanines, luminescence transition metal-ligand complexes, and lanthanides.

Other analytes include analogues of topotecan, such as 10-hydroxycamptothecin, 10,11-methylenedioxycamptothecin, SN-38(7-ethyl-10-hydroxycamptothecin) camptosar, and 9-chloro- 10,11-methylenedioxy camptothecin. The invention is also applicable to any fluorophore which can be excited by a two-photon process. These include analyte-sensing fluorophores such as Fura-2, Quin-2, the SNAFL and SNARF probes, Calcium Green and its analogues, dimethyl amino naphthalene sulfonic acid (DANSYL) probes, 1,6-diphenyl-3-4-5-hexatriene (DPH), cyanines, squaraines, hematoporphyrins, acridines, transition metal-ligand complexes, and lanthanide probes.

The invention is applicable to one-color, two-photon excitation, and also is applicable to two-color, two-photon excitation. Two-photon excitation can be accomplished in several ways. The invention can be performed by using a focused laser beam and the two long wavelength photons which are derived from the same laser beam. Two-photon excitation can also be accomplished utilizing two different laser beams and two different wavelengths or the same wavelength. An advantage of two-color, color, two-photon excitation is the ability to localize the point of excitation at the intersection of the two laser beams. It may also be possible to improve selectivity or sensitivity by the selection of two different wavelengths.

The invention is also applicable to three-photon and other multi-photon excitation. Three-photon excitation has been accomplished in clear media in accordance with the present invention.

The invention will be further described with respect to measurement of the anti-cancer drug topotecan in plasma and whole blood by two-photon excitation, but it will be understood by persons skilled in the art that the invention is also applicable to other drugs capable of multi-photon excitation, as set forth above.

EXAMPLE 1

FLUORESCENCE DETECTION OF THE ANTI-CANCER DRUG TOPOTECAN IN PLASMA AND WHOLE BLOOD BY TWO-PHOTON EXCITATION

Topotecan is a water-soluble topoisomerase inhibitor which displays anti-tumor activity in animals and humans. This new drug has recently been approved by the FDA for chemotherapeutic treatment of ovarian cancers. Treatment with topotecan requires careful control of its concentration to assure effectiveness without excessive toxicity (van Warmerdam et al., "Phase I clinical and pharmacokinetic study of topotecan administered by 24-hour continuous infusion", *J. Clin. Oncology*, 13(7):1768–1776 (1995); and Blaney et al., "Intrathecal administration of topotecan in nonhuman primates", *Cancer Chemother. Pharmacol.*, 36:121–124 (1995)).

Figure 1A:
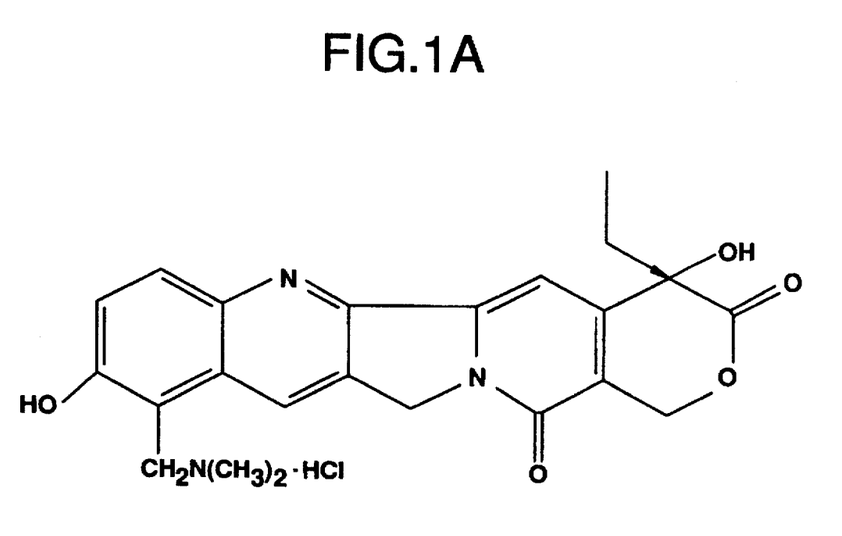
FIG. 1A shows the structural formula of the lactone form of topotecan, an analyte to which one embodiment of the invention is applicable.

Topotecan (FIG. 1A) and its analogues are known to display fluorescence when excited by one-photon near 350–420 nm (Burke et al., "Lipid bilayer partitioning and stability of camptothecin drugs", *Biochem.*, 32:5352-5364 (1993); and Malak et al., "Reduced albumin binding promotes the stability and activity of topotecan in human blood", *Biochem.*, 34:13722–13728 (1995)). However, such wavelengths are inconvenient for clinical monitoring because they are absorbed by tissues, skin and blood, and these wavelengths also result in significant autofluorescence. However, the auto fluorescence from tissues decreases with longer wavelength illumination (i.e., greater than about 600 nm), and tissues are minimally absorbing at wavelengths above 650 nm. These spectral properties of tissues provide the basis for the present invention, and non-invasive diagnostics or imaging based on long wavelength illumination.

Advances in laser technology have resulted in long wavelength lasers with femtosecond pulse widths. The high peak intensity of such sources permits two-photon excitation, that is, the simultaneous absorption of two long wavelength photons to yield the first singlet state observed with UV excitation. Two-photon excitation has been applied in analytical chemistry (Sepaniak et al., "Laser two-photon excited fluorescence detection for high pressure liquid chromatography", *Anal. Chem.*, 49(11):1554–1556 (1977); Steffen et al., "Multipoint measurements in optically dense medial by using two-photon excited fluorescence and a fiber-optic star coupler", *Anal. Chem.*, 215:203–210 (1988); and Wirth et al., "Two-photon excited molecular fluorescence in optically dense media", *Anal. Chem.*, 49(13):2054–2059 (1977)), time-resolved fluorescence (Lakowicz et al., "Trytophan fluorescence intensity and anisotropy decays of human serum albumin resulting from one-photon and two-photon excitation", *Biophys. Chem.*, 45:1–6 (1992); Lakowicz et al., "Time-resolved fluorescence intensity and anisotropy decays of 2,5-diphenyloxazole by two-photon excitation and frequency-domain fluorometry", *Phys. Chem.*, 96:3000–3006 (1992); and Lakowicz et al., "Two photon-induced fluorescence intensity and anisotropy decays of diphenylhexatriene in solvents and lipid bilayers", *J. Fluoresc.*, 2(4):247–258 (1992)), and in fluorescence microscopy (Denk et al., "Two-photon excitation in laser scanning microscopy", *Science*, 248:73–76 (1990); Piston et al., "Time-resolved fluorescence imaging and background rejection of two-photon excitation in laser scanning microscopy", SPIE, 1640:379–388 (1992); and Huang et al., "Theory for two-photon excitation in pattern photobleaching with evanescent illumination"(1993), *Biophys. Chem.*, 47:241-249 (1993)). However, the present invention is directed to the use of two-photon induced fluorescence to detect analytes in animal tissues, such as whole blood. The present example shows that physiologically relevant concentrations of the antibiotic topotecan can be detected by two-photon near infrared (NIR) excitation, both in human plasma and in whole blood. It has been discovered that two-photon induced fluorescence of the numerous possible interferences is not significant compared to the signal observed from micromolar concentrations of topotecan. This provides the basis for using long wavelength two-photon excitation for direct measurements in whole blood and noninvasive detection through skin.

| Abbreviations | |
|---|---|
| PBS | Phosphate buffered saline |
| TD | time-domain |
| FD | frequency-domain |
| TCSPC | time-correlated single photon counting |
| 1PE | one-photon excitation |
| 2PE | two-photon excitation |

Materials and Methods

Chemicals. Topotecan was obtained from the Stehlin Foundation, Houston, Tex., and the National Cancer Institute, Division of Cancer Treatment, respectively. Drugs were in the 20S configuration and were of high purity (>98%) as determined by HPLC assays with fluorescence detection (Burke et al, "The structural basis of camptothecin interactions with human serum albumin: Impact on drug stability", *Med. Chem.*, 37(1):40–46 (1994); Mi et al., "Differential interactions of camptothecin lactone and carboxylate forms with human blood components", *Biochem.*, 33(34):10325–10326 (1994); and Mi et al., "Marked interspecies variations concerning the interactions of camptothecin with serum albumins: A frequency-domain fluorescence spectroscopic study", *Biochem.*, 34(42):12540–12545 (1994)). Drug stock solutions ($2 \times 10^{-3}$M) were prepared in dimethyl sulfoxide (DMSO) and stored in the dark at $-20°$ C. Working solutions of topotecan carboxylate were prepared by a 1:1 dilution of the DMSO stock solution in PBS buffer (pH 10) to a final concentration of $1 \times 10^{-3}$M.

Preparation of Whole Blood. Whole human blood was obtained from a healthy male donor by drawing blood into sterile vacutainers containing either ethylenediaminetetraacetic acid (EDTA) or heparin to prevent clot formation. Human plasma samples were obtained from the Red Cross of Ohio and were used without further processing. Human plasma samples for drug analysis studies were continuously aerated with "blood gas"(MEDIBLEND, Linde Medical Gases, Connecticut) in order to maintain constant pH (7.5±0.1).

Instrumentation. The emission of topotecan was observed using a combination of Corning filters: 3–71 and 4–96 plus a 03FHA020 heat filter. This combination showed a peak transmission of 55% near 530, with over 10% transmission from 440 nm to 580 nm.

Two-photon excitation at 820 nm was provided by a fs mode-locked Tsunami Ti:Sapphire laser from Spectra Physics. The repetition rate of 80 MHZ was held fixed by the Loc-to-Clock accessory. The repetition rate was divided by 8 by the Loc-to-Clock electronics, and used as the 10 MHZ reference signal for the FD instrument. The pulse width was near 80 fs. Two-photon excitation at 730 nm was provided by a pyridine dye laser, 7 ps pulse width, which was synchronously pumped by a mode-locked argon ion laser. Frequency-domain (FD) intensity and anisotropy decays with three-photon excitation were obtained on instrumentation described previously (Lakowicz et al., "Construction and performance of a variable-frequency phase- modulation fluorometer", *Biophys. Chem.*, 21:61–78 (1985); and Laczko et al., "A 10 GHz frequency-domain fluorometer", *Rev. 2 Sci. Instrum.*, 61:2331–2337 (1990)). Time-domain (TD) intensity decays were obtained by time-correlated single photon counting (TCSPC) (Birch et al., "Time-domain fluorescence spectroscopy using time-correlated single-photon counting", *Topics in Fluorescence Spectroscopy*, Vol. 1: Techniques, (J. R. Lakowicz, Ed.), Plenum Publishing, New York, pp.1–95 (1991)) using a R2809 microchannel plate PMT as the detector.

Results

Figure 1B:
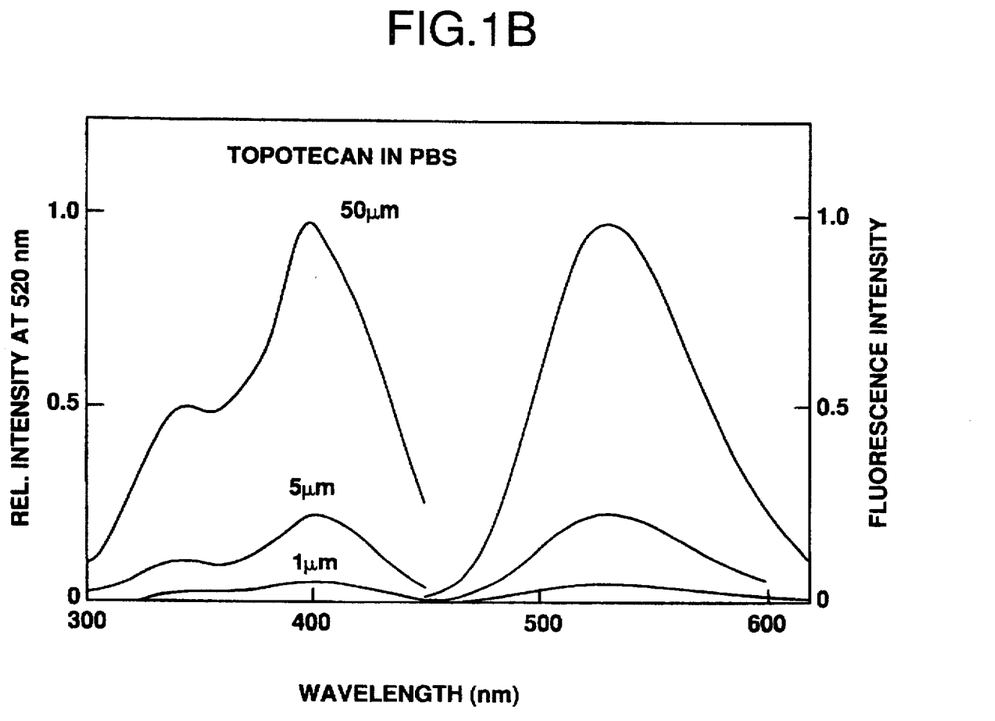
FIG. 1B is a graph showing fluorescence one-photon excitation and emission spectra of topotecan in PBS (1 µm, 5 µm, and 50 µm). The curves on the left are the excitation spectra observed with a 520 nm emission wavelength.
Figure 2:
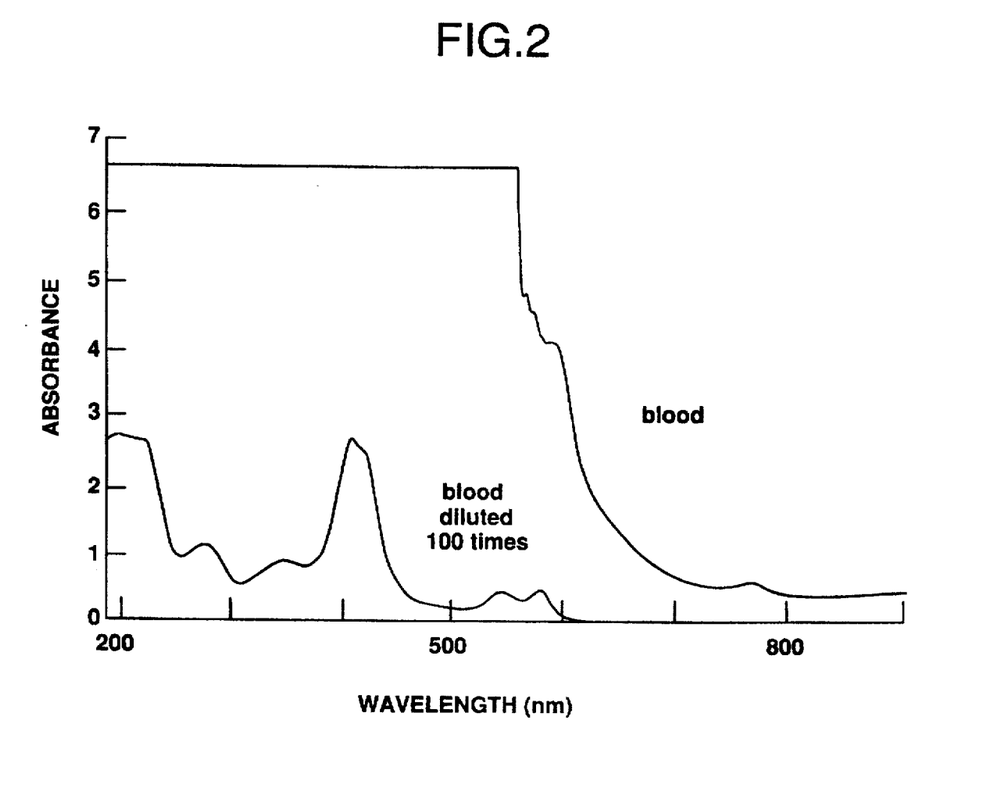
FIG. 2 is a graph showing absorption spectra of whole blood and whole blood diluted 100-fold.

Excitation and emission spectra of topotecan are shown in FIG. 1B. One-photon photon excitation of topotecan requires excitation at wavelengths below 400 nm, resulting in an emission centered near 520 nm. The single photon excitation wavelengths and emission spectra of topotecan (FIG. 1B) overlap with the absorption of human plasma and whole blood (FIG. 2). These spectra suggest that it would be difficult, if not impossible, to detect topotecan with one-photon excitation.

Figure 3:
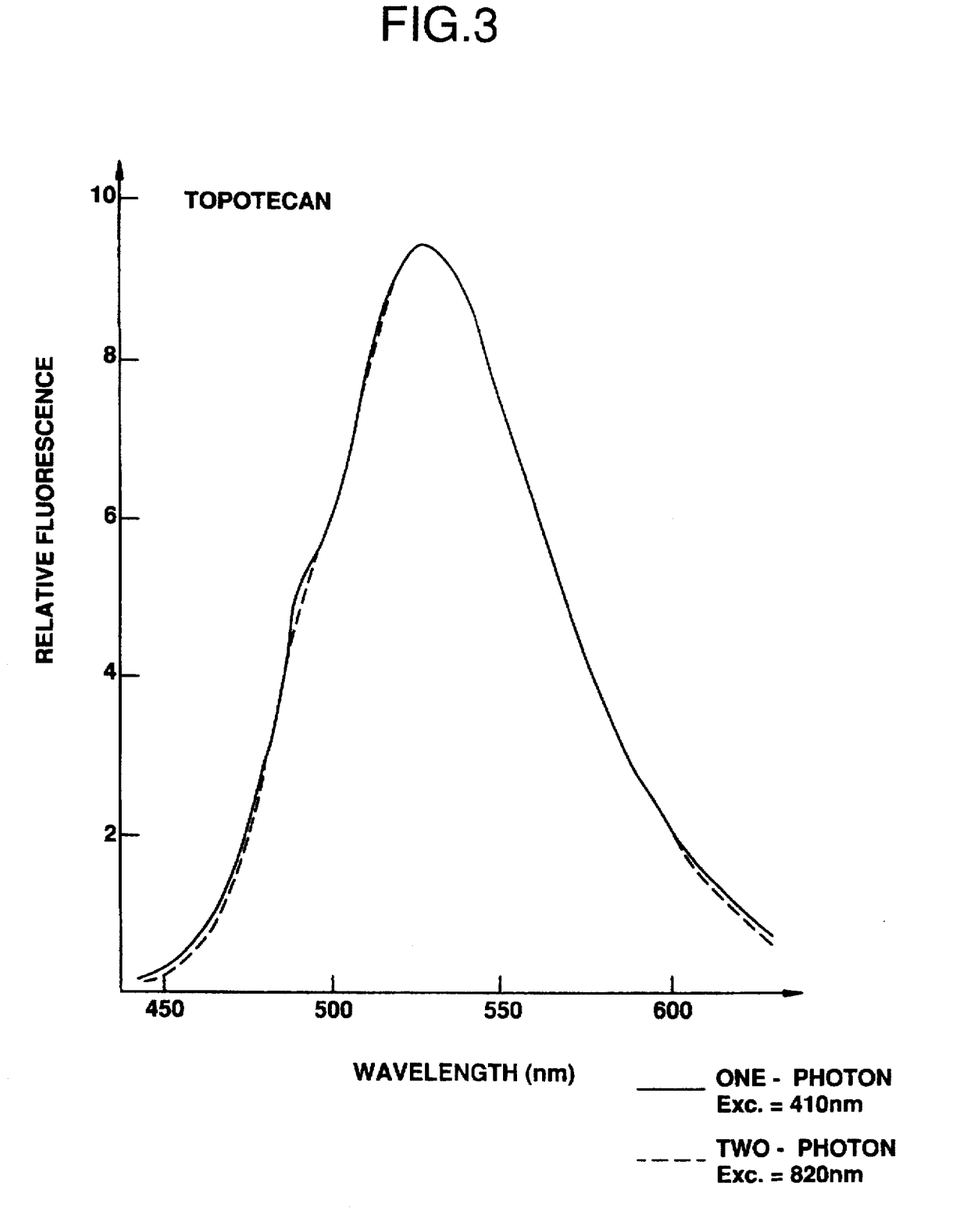
FIG. 3 is a graph showing emission spectra of 5 µm topotecan in for excitation at 410 nm in PBS or for excitation at 820 nm in plasma.
Figure 4:
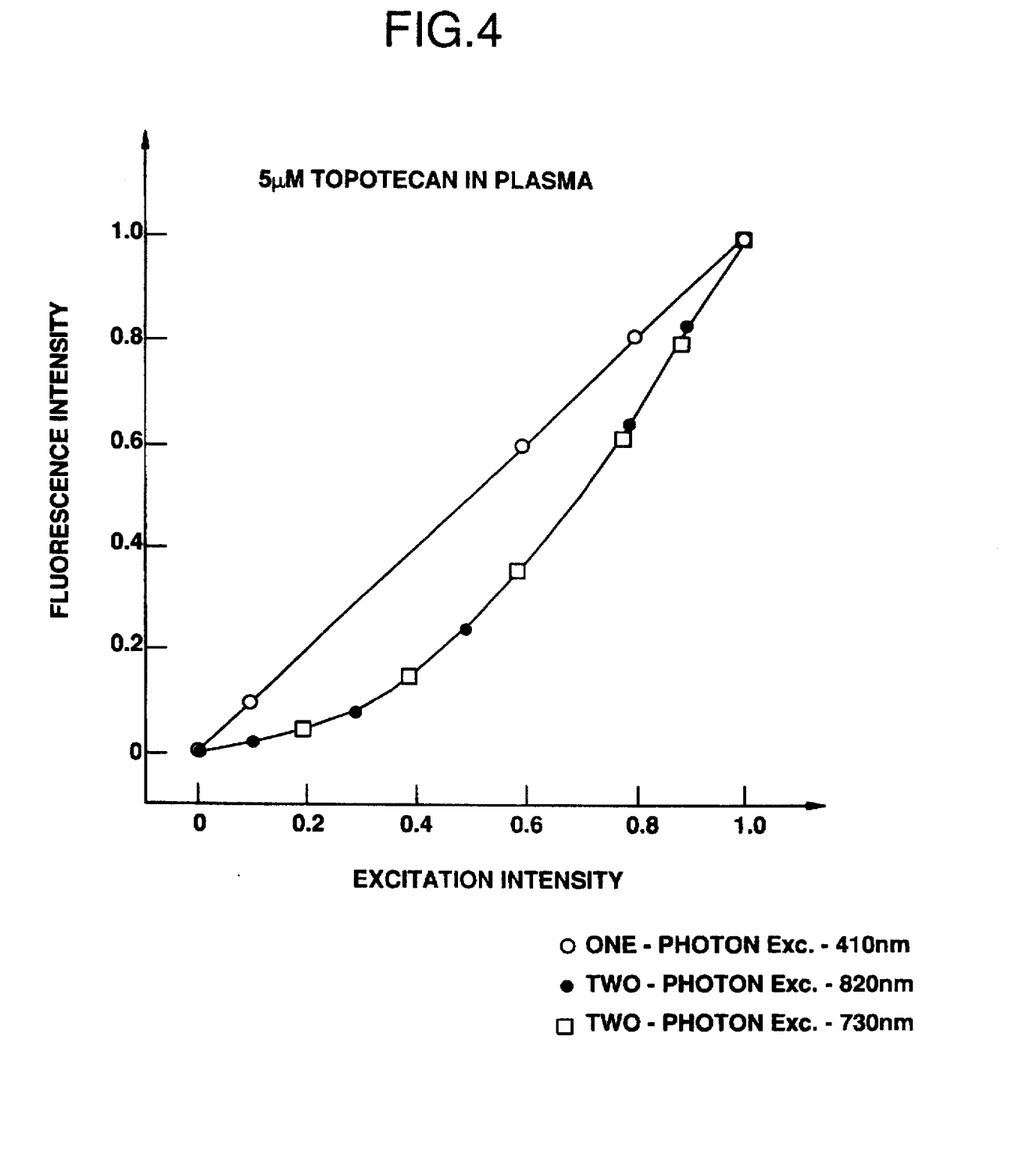
FIG. 4 is a graph showing dependence of topotecan emission intensity in plasma on the excitation intensity at 410, 730 and 820 nm. The intensities were normalized to unity at the highest excitation intensities.

The emission spectra of topotecan in plasma excited with one- and two-photon excitation (FIG. 3) was examined. Plasma was selected for the initial experiments because one can readily remove the erythrocytes in a clinical setting. The emission spectra of topotecan in plasma were identical for excitation at 410 nm in PBS and for excitation at 820 nm in plasma (FIG. 3). At these wavelengths, the emission intensities depended linearly and quadratically on the intensity of the incident light, respectively (FIG. 4). The same emission spectrum was observed for excitation at 730 nm and 820 nm (not shown), and the topotecan intensity depended quadratically on the incident intensity at 730 nm (FIG. 4). These results indicate that the emission of topotecan is due to one-photon excitation (1PE) at 410 nm, and due to two-photon excitation (2PE) at 730 nm and 820 nm.

Figure 5:
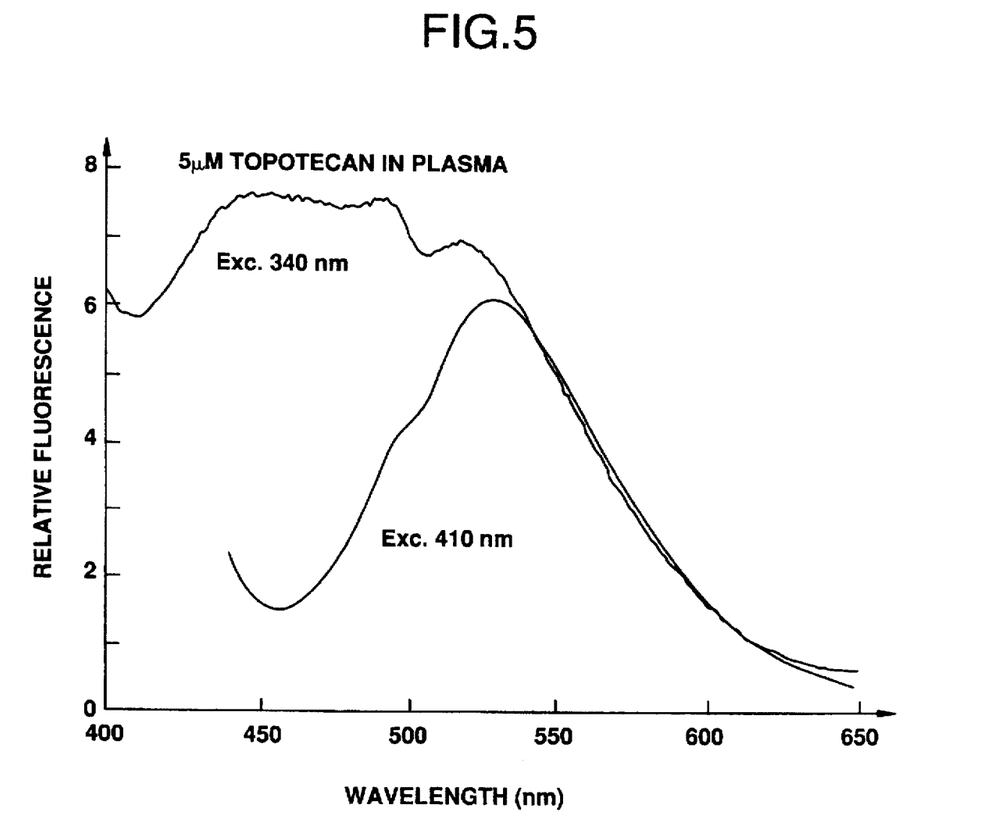
FIG. 5 is a graph showing emission spectra of 5 µm topotecan in plasma for excitation at 340 and 410 nm.

The advantages of two-photon excitation for detection of topotecan are shown in FIG. 5, which shows emission spectra for excitation at 340 nm and 410 nm. At 340 nm, the background fluorescence from the plasma essentially overwhelms the emission from topotecan. At 410 nm, one can detect the spectral shape of topotecan but one notices the increase amount of auto-fluorescence and/or scattered light on the short wavelength side of the emission spectrum. Comparison of the emission spectrum in plasma with 410 nm excitation (FIG. 5) with that observed for topotecan with two-photon excitation at 820 nm in plasma (FIG. 3) demonstrates a lower level of auto-fluorescence in plasma with two-photon excitation.

Figure 6:
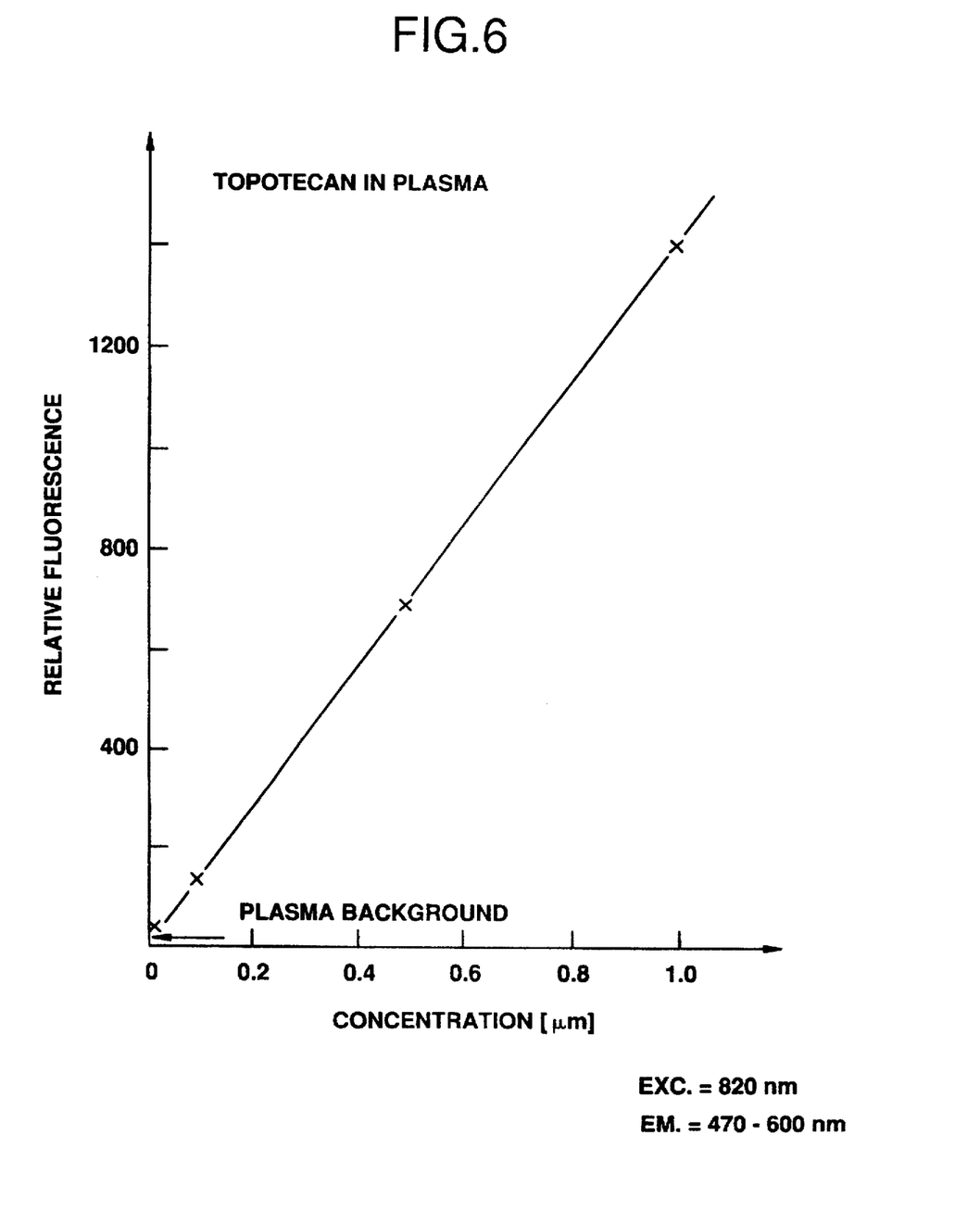
FIG. 6 is a graph showing concentration-dependent emission intensity of topotecan in plasma for excitation at 820 nm.

The ability to detect clinically relevant concentrations of topotecan using two-photon excitation was tested. The concentration-dependent intensity of topotecan in plasma with 820 nm excitation is shown in FIG. 6. Remarkably, concentrations down to 0.2 µM were readily detected (ten-fold over background), and the detection limit (two-fold over background) was near 0.05 µM topotecan.

Figure 7:
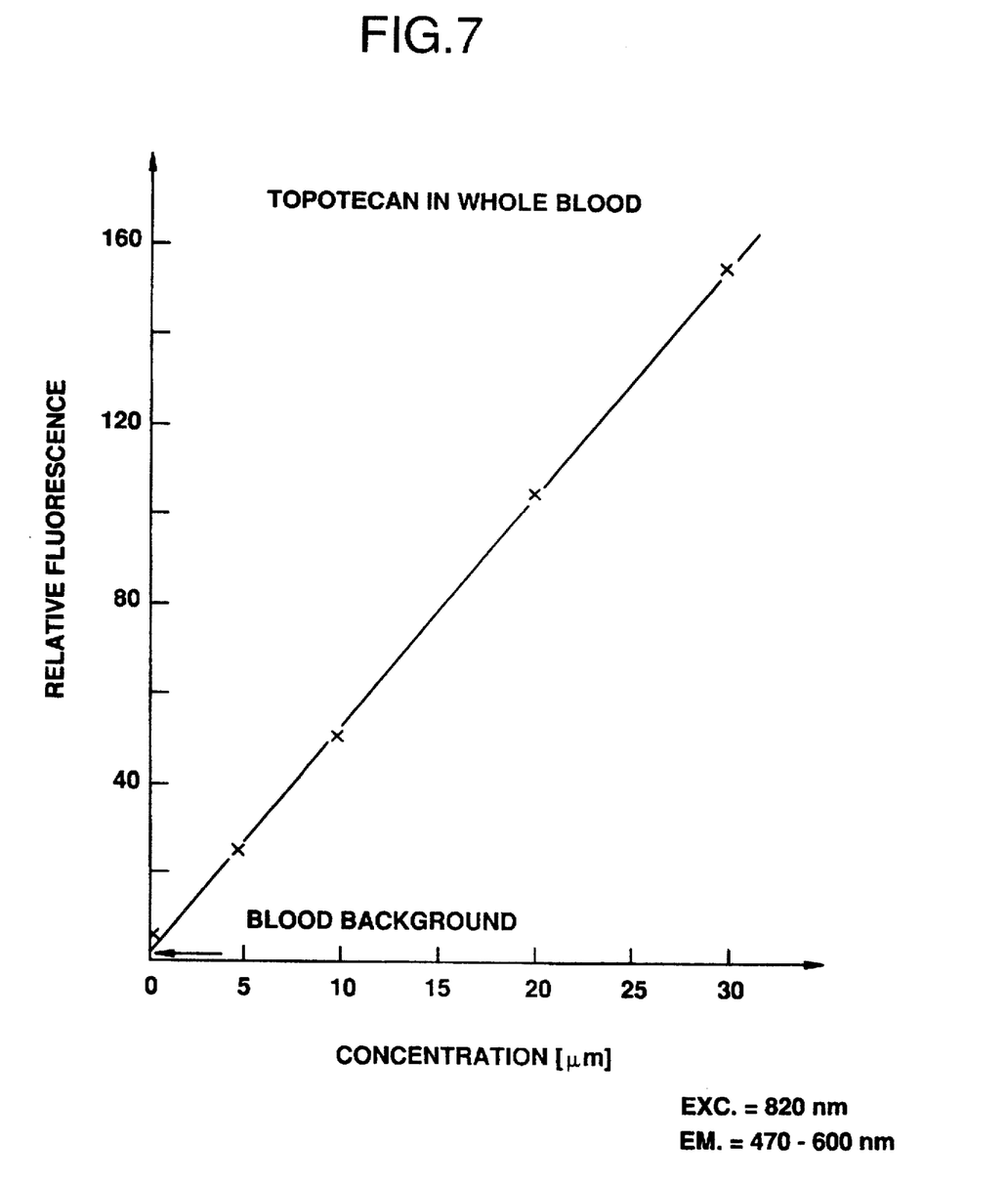
FIG. 7 is a graph showing concentration-dependent intensity of topotecan in whole blood for excitation at 820 nm.

Topotecan also was detected in whole blood with 820 nm excitation (FIG. 7). In this case the signal was weaker, probably due to reabsorption of the topotecan emission by blood (FIG. 2). Nonetheless, the signal was linearly dependent on topotecan concentration, and the detection limit was about 1 µM. It was difficult to record on emission spectrum of topotecan in whole blood, but the spectrum observed appeared to be characteristic of topotecan (not shown).

Figure 8A:
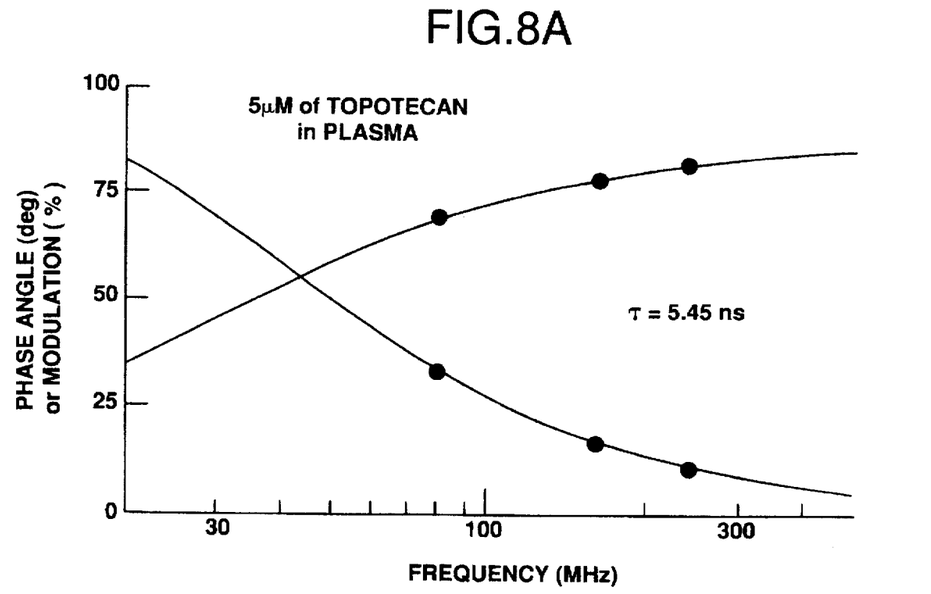
FIG. 8 graphically displays frequency-domain intensity decay of topotecan in PBS and plasma with 820 nm excitation.
Figure 8B:
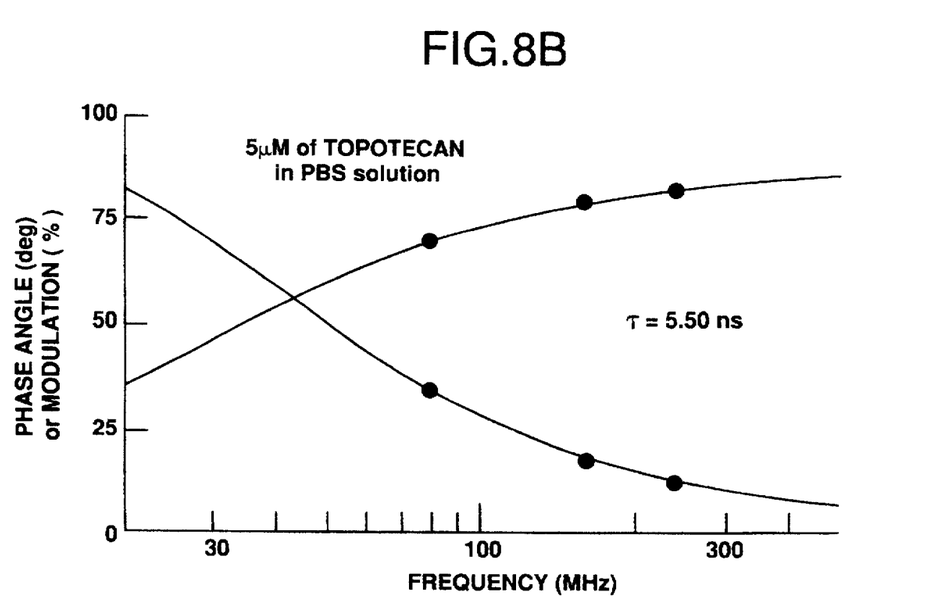
Figure 9:
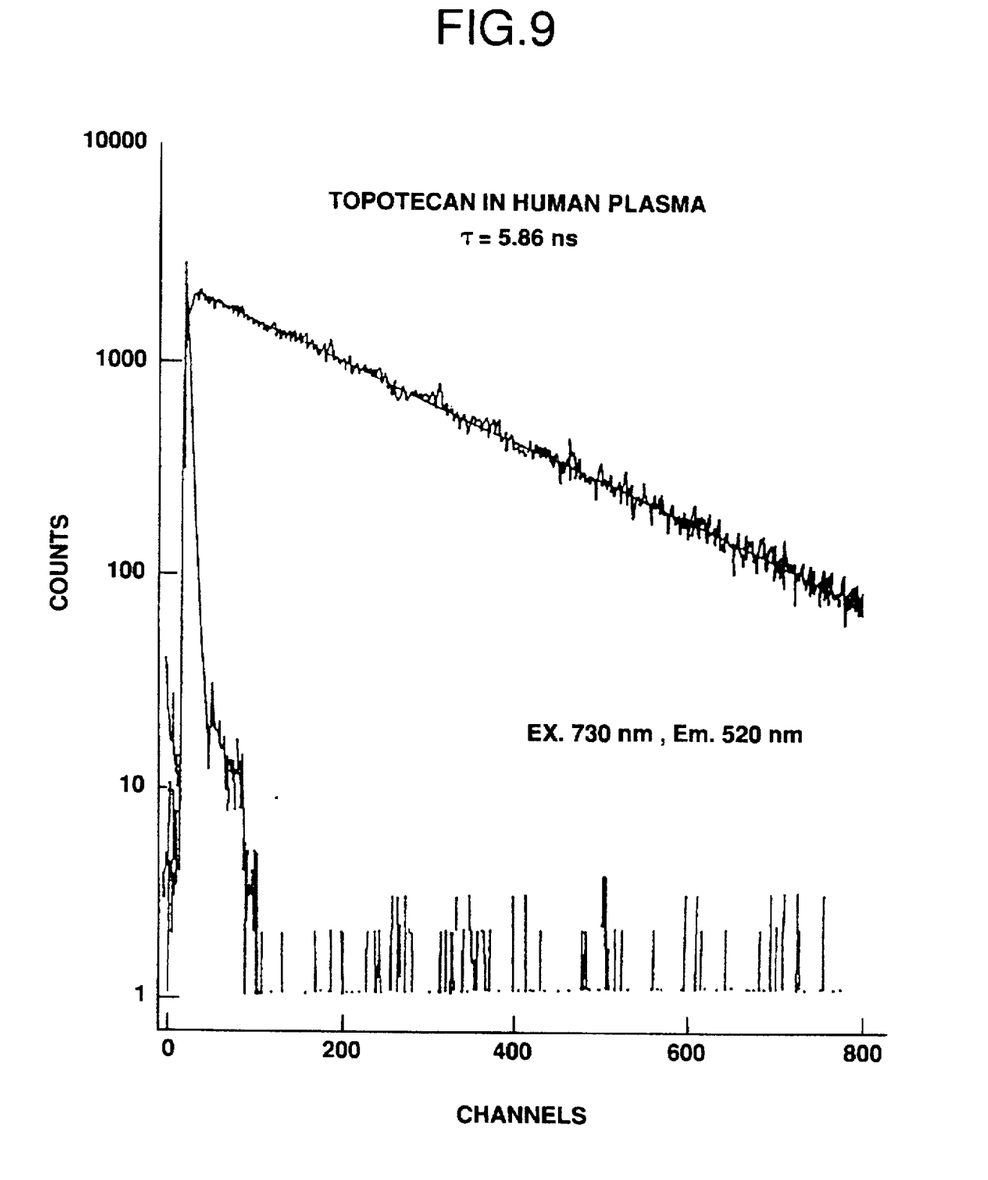
FIG. 9 graphically displays time-domain intensity decay for topotecan in plasma for excitation at 730 nm.
Figure 10:
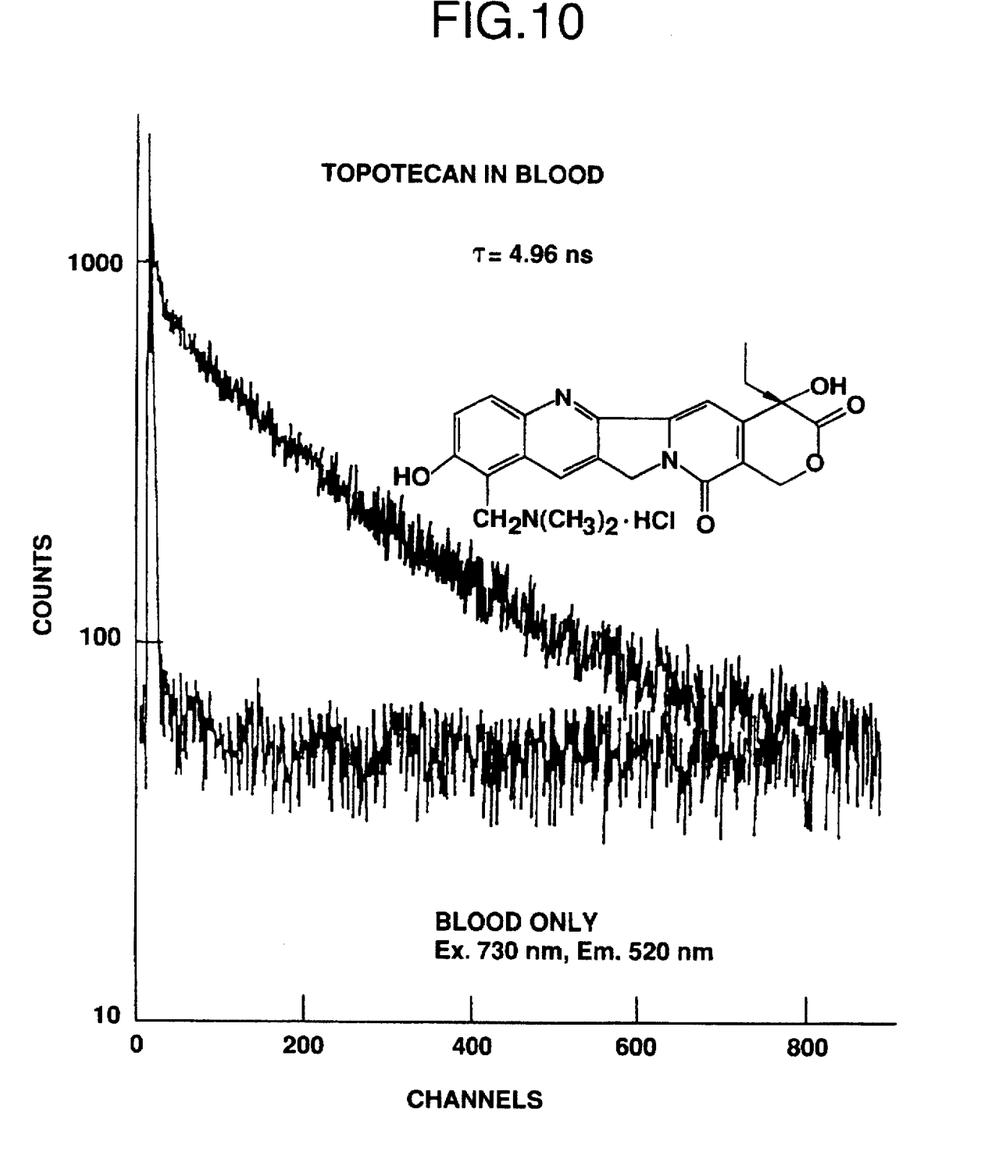
FIG. 10 graphically displays time-domain intensity for topotecan in whole blood for excitation at 730 nm.

Blood and plasma contain numerous chromophores absorbing from 365 nm to 410 nm, and some of these may be expected to display 2PE at 730 nm or 820 nm. To confirm that the emission was in fact due to topotecan, the fluorescence lifetimes were examined. Frequency-domain lifetime data are shown in FIG. 8 for 820 nm excitation. Similar decay times were observed from two-photon excitation in plasma (top) or in PBS (bottom). The observed decay times are comparable to those observed for topotecan with one-photon excitation (5.8 ns). The decay times were also measured by TCSPC, in plasma (FIG. 9) and whole blood (FIG. 10) with 730 nm excitation. Once again, the decay times were characteristic of topotecan. These lifetimes indicate that topotecan was the species responsible for the observed emission.

In summary, the anti-cancer drug topotecan was detected in human plasma and whole blood using two-photon excitation at 730 nm or 820 nm. These wavelengths are longer than the main absorption bands of hemoglobin. Two-photon excitation of topotecan was demonstrated by a quadratic dependence of the emission intensity on the incident power, as compared to a linear dependence for one-photon excitation at 410 nm. The observed emission centered near 520 nm was shown to be topotecan from the similarity of the emission spectrum and decay times observed for one-photon and two-photon excitation. The topotecan detection limits of 0.05 µM and 2 µM in plasma and whole blood, respectively, are comparable to the concentration used for treatment of cancers. Because skin, blood and tissues are translucent at long wavelengths, these results provide the basis for homogeneous or noninvasive clinical sensing with two-photon excitation.

Discussion

The data described above indicate that at micromolar concentrations, the emission of topotecan resulting from two-photon excitation at 730 nm and 820 nm is the dominant chromophore in whole blood or plasma. This suggests that topotecan displays a high cross-section for two-photon excitation compared to other endogenous biochemical fluorophores. Accordingly, the invention is applicable to other drugs with high two-photon cross-sections. Given the increasing availability of picosecond and femtosecond laser sources, and the minimal health risks associated with long wavelength illumination, the invention provides the basis for two-photon induced fluorescence for noninvasive detection of drugs and other analytes.

Because various modifications, variations and changes can be made the described embodiments, it is intended that all matter in the foregoing description and shown in the drawings be interpreted as illustrative and not in a limiting sense.

We claim:

1. A method of measuring an analyte present in animal tissue, comprising:
   providing animal tissue containing an analyte which is two-photon-excitable at a first wavelength at which said animal tissue is substantially non-absorbing, which analyte fluoresces at a second wavelength upon being two-photon-excited at said first wavelength;
   irradiating said animal tissue with radiation at said first wavelength so as to excite said analyte through absorption by said analyte of two photons of said radiation at said first wavelength, wherein excitation of said analyte results in a fluorescent emission from said analyte of radiation at said second wavelength;
   detecting said emission at said second wavelength; and
   determining the concentration of analyte based on the detected emission.

2. The method of claim 1, wherein, in said determining step, intensity of said emission at said second wavelength is measured, and wherein said concentration of said analyte is determined utilizing the measured intensity of said emission.

3. The method of claim 1, wherein, in said determining step, lifetime of said emission at said second wavelength is measured, and wherein said concentration of said analyte is determined utilizing the measured lifetime of said emission.

4. The method of claim 1, wherein said first wavelength is greater than about 400 nm.

5. The method of claim 4, wherein said first wavelength is greater than about 600 nm.

6. The method of claim 5, wherein said first wavelength is less than about 1,000 nm.

7. The method of claim 6, wherein said second wavelength is less than about 1000 nm.

8. The method of claim 1, wherein said analyte is a drug.

9. The method of claim 1, wherein said analyte is topotecan.

10. The method of claim 9, wherein the first wavelength is selected from the group consisting of about 730 nm and about 820 nm.

11. The method of claim 10, wherein said second wavelength is about 525 nm.

12. The method of claim 1, wherein the analyte is a fluorescence substance utilized in fluorescence measurements, selected from the group consisting of fluorosceins, rhodamines, calcium-sensitive fluorophores including Fura-2, pH-sensitive fluorophores including the semiapthofluoresceins and semiapthorhodamines, sodium-sensitive fluorophores including Sodium Green and SBFI, potassium-sensitive fluorophores including PBFI, cyanines, luminescence transition metal-ligand complexes, and lanthanides.

13. The method of claim 1, wherein said analyte is selected from the group consisting of 10-hydroxycamptothecin, 10,11-methylenedioxycamptothecin, SN-38(7-ethyl-10-hydroxycamptothecin) camptosar, and 9-chloro-10,11-methylenedioxy camptothecin.

14. The method of claim 1, wherein said analyte is selected from the group consisting of Fura-2, Quin-2, SNAFL probes, SNARF probes, Calcium Green, DANSYL probes, DPH, cyanines, squaraines, hematoporphyrins, acridines, transition metal-ligand complexes, and lanthanide probes.

15. A method of measuring an analyte present in animal tissue, comprising:
   providing animal tissue containing an analyte which is excitable by a plurality of photons at a first wavelength at which said animal tissue is substantially non-absorbing, which analyte fluoresces at a second wavelength upon being excited at said first wavelength;
   irradiating said animal tissue with radiation at said first wavelength so as to excite said analyte through absorption by said analyte of said plurality of photons of said radiation at said wavelength, wherein excitation of said analyte results in a fluorescent emission from said analyte of radiation at said second wavelength;
   detecting said emission at said second wavelength; and
   determining the concentration of analyte based on the detected emission.

16. The method of claim 15, wherein said analyte is excitable by at least three photons at said first wavelength.

17. A method of measuring an analyte present in a material, comprising:
   providing material containing an analyte which is excitable by a plurality of photons at a plurality of wavelengths at which said material is substantially non-absorbing, which analyte fluoresces at a different wavelength upon being excited at said plurality of wavelengths;
   irradiating the material with radiation at said plurality of wavelengths so as to excite said analyte through absorption by said analyte of a plurality of photons of said radiation at said plurality of wavelengths, wherein excitation of said analyte results in a fluorescent emission from said analyte of radiation at said different wavelength;
   detecting said emission at said different wavelength; and
   determining the concentration of analyte based on the detected emission.

18. The method of claim 1, wherein said analyte is one-photon excitable at a wavelength which is absorbed by said animal tissue.

19. The method of claim 1, wherein said analyte is one-photon excitable at a wavelength which is absorbed by said animal tissue so as to result in an emission which is absorbed by said animal tissue.

20. The method of claim 1, wherein said animal tissue is optically dense.

21. The method of claim 1, wherein said tissue is whole tissue.

22. The method of claim 1, wherein said irradiating said animal tissue, and detecting said emission, take place through skin of an animal.

* * * * *

UNITED STATES PATENT AND TRADEMARK OFFICE
CERTIFICATE OF CORRECTION

PATENT NO. : 5,759,767
DATED : June 2, 1998
INVENTOR(S) : Joseph R. LAKOWICZ

It is certified that error appears in the above-identified patent and that said Letters Patent is hereby corrected as shown below: On the title page, Column 1 under item [56] References Cited, U.S. Patent Documents, insert
--5,062,428    11/1991    Chance.......128/664--.

Signed and Sealed this

Sixth Day of July, 1999

Attest:

Q. TODD DICKINSON

*Attesting Officer*    Acting Commissioner of Patents and Trademarks